United States Patent [19]

Beriger et al.

[11] Patent Number: 5,013,745

[45] Date of Patent: May 7, 1991

[54] NEMATICIDAL COMPOSITIONS

[75] Inventors: Ernst Beriger, Allschwil, Switzerland; Wolfgang Eckhardt, Lörrach, Fed. Rep. of Germany

[73] Assignee: Ciba-Geigy Corporation, Ardsley, N.Y.

[21] Appl. No.: 408,838

[22] Filed: Sep. 18, 1989

[30] Foreign Application Priority Data

Sep. 23, 1988 [CH] Switzerland .................. 3536/88

[51] Int. Cl.$^5$ ............. C07D 285/125; C07D 271/113; C07D 413/04; A01N 43/82
[52] U.S. Cl. .................................. 514/364; 514/363; 548/136; 548/144
[58] Field of Search ................ 548/136, 144; 514/363, 514/364

[56] References Cited

U.S. PATENT DOCUMENTS

| | | | |
|---|---|---|---|
| 3,770,754 | 11/1973 | Parseens | 260/302 |
| 4,259,104 | 3/1981 | Edwards | 548/144 |
| 4,454,147 | 6/1984 | Di Menna et al. | 424/270 |
| 4,861,787 | 8/1989 | Beriser | 514/363 |

FOREIGN PATENT DOCUMENTS

| | | | |
|---|---|---|---|
| 239047 | 9/1987 | European Pat. Off. | 548/136 |
| 8607590 | 12/1986 | PCT Int'l Appl. | 71/90 |
| 1429725 | 3/1976 | United Kingdom | 71/90 |

OTHER PUBLICATIONS

J. Org. Chemistry, vol. 26, #1, 88-95 (1961).
O. Turilli, Annali di Chimica, 53, 1687-1698 (1963).

*Primary Examiner*—Robert Gerstl
*Attorney, Agent, or Firm*—George R. Dohmann; Edward McC. Roberts

[57] ABSTRACT

2-Mercapto-1,3,4-oxadiazoles and 2-mercapto-1,3,4-thiadiazoles of the formula I

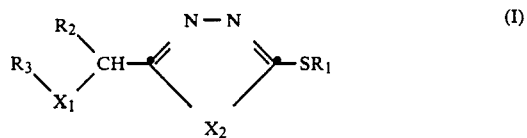

in which $X_1$ and $X_2$ independently of one another are oxygen or sulfur, $R_1$ is difluoromethyl or 3,4,4-trifluoro-3-butenyl, $R_2$ is hydrogen or $C_1$-$C_3$alkyl and $R_3$ is hydrogen, $C_1$-$C_5$alkyl which is unsubstituted or substituted by halogen or $C_1$-$C_3$alkoxy, $C_3$-$C_7$alkenyl which is unsubstituted or substituted by halogen or $C_1$-$C_3$alkoxy, $C_3$-$C_7$alkynyl which is unsubstituted or substituted by halogen or $C_1$-$C_3$alkoxy, or phenyl which is unsubstituted or substituted by halogen, $NO_2$, $CF_3$, $C_1$-$C_3$alkyl or $C_1$-$C_3$alkoxy, or wherein, furthermore, $R_2$ and $R_3$ together can form the methylene chain $(-CH_2-)_n$ as a constituent of a 5- or 6-membered ring with the heteroatom $X_1$, in which n is 3 or 4, and processes for the preparation of the compounds of the formula I are described.

The compounds of the formula I have nematicidal properties. Nematicidal compositions which contain at least one active substance of the formula I as the active substance and furthermore methods of using the active substances and the compositions for controlling nematodes are described.

17 Claims, No Drawings

NEMATICIDAL COMPOSITIONS

The present invention relates to novel substituted 2-mercapto-1,3,4-oxadiazoles and 2-mercapto-1,3,4-thiadiazoles, their preparation and nematicidal compositions containing at least one of these compounds as the active substance. The invention relates to the use of 2-mercapto-1,3,4-oxadiazoles and of 2-mercapto-1,3,4-thiadiazoles and compositions for controlling nematodes, in particular nematodes which are harmful to plants.

The 2-mercapto-1,3,4-oxadiazoles and 2-mercapto-1,3,4-thiadiazoles according to the invention are those of the general formula I

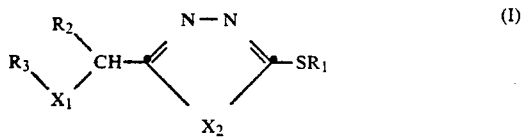

in which $X_1$ and $X_2$ independently of one another are oxygen or sulfur, $R_1$ is difluoromethyl or 3,4,4-trifluoro-3-butenyl, $R_2$ is hydrogen or $C_1$–$C_3$-alkyl and $R_3$ is hydrogen, $C_1$–$C_5$alkyl which is unsubstituted or substituted by halogen or $C_1$–$C_3$alkoxy, $C_3$–$C_7$alkenyl which is unsubstituted or substituted by halogen or $C_1$–$C_3$alkoxy, $C_3$–$C_7$alkynyl which is unsubstituted or substituted by halogen or $C_1$–$C_3$alkoxy, or phenyl which is unsubstituted or substituted by halogen, $NO_2$, $CF_3$, $C_1$–$C_3$alkyl or $C_1$–$C_3$-alkoxy, wherein, furthermore, $R_2$ and $R_3$ together can form the methylene chain ($-CH_2-$) as a constituent of a 5- or 6-membered ring with the heteroatom $X_1$, in which n is 3 or 4, and salts of one of these compounds.

Alkyl as an independent radical or as part of another group, such as alkoxy, is to be understood as meaning straight-chain or branched alkyl groups. These include the methyl, ethyl and normal and isomeric propyl, butyl and pentyl groups. Halogen-substituted alkyl is a mono- or perhalogenated alkyl radical, for example $CHCl_2$, $CH_2F$, $CCl_3$, $CH_2Cl$, $CHFCH_3$, $CH_2CH_2Br$, $CF_2CF_3$, $C_2Cl_5$, $CH_2Br$, $CHBrCl$ and the like, and preferably $CHF_2$. Alkenyl is, for example, 1-propenyl, allyl, 1-butenyl, 2-butenyl or 3-butenyl, as well as chains with several double bonds. Halogenoalkenyl is, for example, 3,4,4-trifluoro-3-buten-1-yl. Alkynyl is, for example, propin-2-yl, butin-1-yl, butin-2-yl, pentin-4-yl and the like. Halogen is fluorine, chlorine, bromine or iodine, preferably fluorine, chlorine or bromine.

Examples of salt-forming acids are, amongst the inorganic acids, hydrogenhalide acids, such as hydrofluoric acid, hydrochloric acid, hydrobromic acid or hydroiodic acid, and furthermore sulfuric acid, phosphoric acid, phosphorous acid and nitric acid, and, amongst the organic acids, acetic acid, trifluoroacetic acid, trichloroacetic acid, propionic acid, glycolic acid, thiocyanic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid, 2-phenoxybenzoic acid or 2-acetoxybenzoic acid.

Oxidiazole and thiadiazole derivatives which are described as having a nematicidal action are already known. Thus, U.S. Pat. No. 3,770,754 discloses those compounds having a 1,2,4-position of the heteroatoms, whereas 1,3,4-thiadiazole derivatives in which, in contrast to the compounds according to the invention, the heterocyclic radical is substituted by a chlorine atom instead of the mercapto groups are described in U.S. Pat. No. 4,454,147. To date, these known compounds have not been able to meet completely the requirements imposed on them in practice as nematicides. Oxadiazole derivatives having a fungicidal activity are furthermore described in German Offenlegungsschrift 2,361,613. However, none of these compounds which fall within the scope of formula I according to the invention are mentioned expressly in that specification.

By providing the compounds of the formula I according to the invention, it has now been possible to make a useful contribution towards controlling plant nematodes which cause considerable agricultural damage to plants. Harvest losses in crop plants, for example potatoes, cereals, beet, rape, cabbage, tobacco, soybean, cotton and vegetables, and damage in tree nurseries and ornamental plant growing, can in this way be checked in a lasting manner. The compounds according to the invention are distinguished here in particular in effectively controlling soil nematodes which are parasites on roots, for example those of the genera Heterodera and Globodera (cyst-forming nematodes), Meloidogyne (root knot nematodes) and of the genera Radopholus, Pratylenchus, Tylenchulus, Longidorus, Trichodorus and Xiphinema. The nematode genera Ditylenchus (*stem parasites*), Aphelenchoides (*leaf nematodes*) and Anguina (*blossom nematodes*) can furthermore be controlled effectively using the active substances according to the invention.

Particularly harmful nematode species of the genus Meloidogyne, for example *Meloidogyne incognita*, and of the genus Heterodera, for example *Heterodera glycines* (*soybean cyst nematode*), and furthermore of the genus Globodera, for example *Globodera rostochiensis* (*potato cyst nematode*), as well as representatives of migrating endoparasites, for example *Pratylenchus penetrans* or *Radopholus similis*, and representatives of ectoparasites, for example *Trichodorus spp.* and *Xiphinema spp.*, can preferably be controlled successfully using the active substances of the formula I.

The novel active substances can be employed cumulatively, preventatively or systemically for controlling the plant nematodes and for keeping the plants healthy. During this use, they display a widely diverse activity against the various nematode species and thus meet the requirements of practice. The nematicidal mode of action of the compounds according to the invention is advantageously accompanied by a low phytotoxicity, whereupon the generally desirable reduction in environmental pollution is particularly taken into account.

In the context of the present invention, preferred 2-mercapto-1,3,4-oxadiazoles are those of the formula Ia

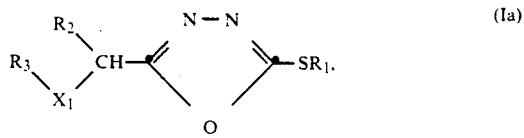

in which $R_1$ is difluoromethyl, $R_2$ is hydrogen and $R_3$ is methyl, or in which $R_2$ and $R_3$ together form the methylene chain ($-CH_2-$)$_3$, as a constituent of a tetrahydrofuran-2-yl or tetrahydrothienyl ring.

2-Difluoromethylthio-5-(tetrahydrofuran-2-yl)-1,3,4-oxadiazole is preferred here as an individual compound.

Those 2-mercapto-oxadiazoles of the formula Ia in which $R_1$ is 3,4,4-trifluoro-3-butenyl, $R_2$ is hydrogen and $R_3$ is methyl, or in which $R_2$ and $R_3$ together form the methylene chain ($-CH_2-$)$_3$, as a constituent of a tetrahydrofuran-2-yl or tetrahydrothienyl ring, are also preferred.

2-(3,4,4-Trifluoromethyl-3-butenylthio)-5-(tetrahydrofuran-2-yl)-1,3,4-oxadiazole is preferred here as an individual compound.

Preferred 2-mercapto-1,3,4-thiadiazoles are furthermore those of the formula Ib

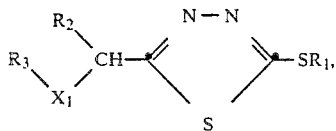

in which $R_1$ is difluoromethyl, $R_2$ is hydrogen and $R_3$ is $C_1$-$C_3$alkyl which is unsubstituted or substituted by halogen, or phenyl which is unsubstituted or substituted by halogen.

2-Difluoromethylthio-5-methoxymethyl-1,3,4-thiadiazole and 2-difluoromethylthio-5-(4-chlorophenoxymethyl)-1,3,4-thiadiazole are preferred here as individual compounds.

The compounds of the formula I are prepared according to the invention by (a) reacting, in a condensation reaction, a compound of the formula II

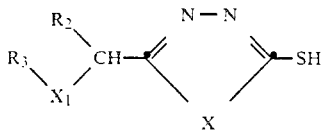

or a compound of the formula III

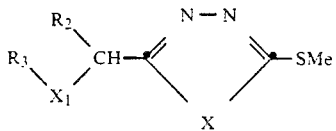

with a compound of the formula IV

Hal-$R_1$     (IV)

an inert solvent or solvent mixture at room temperature or at elevated temperature, if appropriate in the presence of a catalyst and if appropriate under increased pressure, the reaction of a compound of the formula II proceeding in the presence of a base, or (b) reacting, in an addition reaction, a compound of the formula II

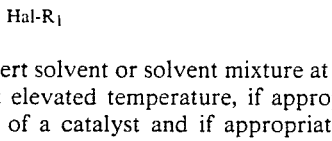

with a compound of the formula V

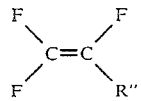

in an inert solvent or solvent mixture at elevated temperature, if appropriate in the presence of a catalyst and if appropriate under increased pressure, this reaction leading to a compound of the formula Ic

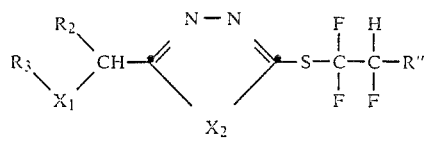

or to a compound of the formula Id

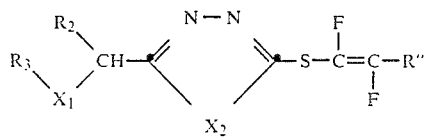

in which, in the abovementioned formulae II, III, Ic, Id, Iv and V, Me is an alkali metal or ammonium, Hal is halogen, preferably chlorine, bromine or iodine, and R″ is fluorine or trifluoromethyl, whilst $R_1$, $R_2$, $R_3$, $X_1$ and $X_2$ are as defined under formula I.

Solvents or diluents which are suitable for the preparation of the active substances according to the invention are, for example, ethers and ether-like compounds, such as dialkyl ethers (diethyl ether, diisopropyl ether, tert.butyl methyl ether and the like), anisole, dioxane and tetrahydrofuran; aliphatic and aromatic hydrocarbons, such as benzene, toluene and petroleum ether; halogenated hydrocarbons, such as chlorobenzene, methylene chloride, chloroform, ethylene chloride, carbon tetrachloride and tetrachloroethylene; nitriles, such as acetonitrile and propionitrile; N,N-dialkylated amides, such as dimethylformamide; dimethylsulfoxide, ketones, such as acetone, diethyl ketone and methyl ethyl ketone, as well as water and alcohols, for example methanol, ethanol, isopropanol or butanol; and quite generally mixtures of such solvents with one another.

Possible bases are organic and inorganic bases; for example, preferably, tertiary amines, such as trialkylamines (trimethylamine, triethylamine, tripropylamine and the like), and oxides, hydroxides, carbonates and bicarbonates of alkali and alkaline earth metals (for example CaO, BaO, NaOH, KOH, Ca(OH)$_2$, KHCO$_3$, NaHCO, Ca(HCO$_3$)$_2$, K$_2$CO$_3$, Na$_2$CO$_3$ and the like), and furthermore acetates, for example CH$_3$COONa or CH$_3$COOK. Alkali metal alcoholates, for example sodium ethylate, sodium propylate, potassium tert.butylate or sodium ethylate, are moreover also suitable as bases.

The addition of catalytic amounts of a crown ether, for example 18-crown-6 or 15-crown-5, has a favourable effect on the course of the reaction in the preparation processes. The catalytic use of tetraalkylamine salts, for example tetraalkylammonium chlorides or bromides, preferably tetra-n-butylammonium bromide, has furthermore proved to be advantageous for the same purpose. Alkali metal iodides, preferably potassium iodide, can moreover advantageously be employed as catalysts. In the preparation processes, the reaction temperatures are 10° to 90° C., preferably 30° to 80° C. 1 to 20 bar, preferably 6 to 14 bar, are decisive for the pressure conditions during the course of the reaction.

The starting compounds of the formula II are known in some cases and novel in some cases. The novel compounds of the formulae mentioned are intermediates for the preparation of useful nematocidal active substances (see Tables 0–3) and thus form a constituent of the present invention.

The starting compounds of the formula Ia and Ib can be prepared by known methods as follows:

(a) The 2-mercapto-1,3,4-oxadiazoles can be obtained by adding carbon disulfide to a solution of the correspondingly substituted hydrazide in alcoholic-aqueous potassium hydroxide and heating the reaction mixture for some hours. Solvents which are used here are alcohols, for example ethyl alcohol or n-amyl alcohol. The free mercapto compounds are obtained by acidification of the potassium salts formed [c.f. J. Am. Chem. Soc. 78, 4975–4978 (1956)]. The 2-mercapto-1,3,4-oxadiazoles can furthermore be obtained by reaction of the corresponding acyl hydrazide with thiophosgene in an inert solvent, for example dioxane [c.f. J. Org. Chem. 26, 88–95 (1961)].

(b) The 2-mercapto-1,3,4-thiadiazoles can be obtained by treatment of the correspondingly substituted acyl-potassium dithiocarbazate with concentrated sulfuric acid at −5° to 10° C. [c.f. J. prakt. Chem. 93, 49 (1916); J. Org. Chem. 23, 1021 (1958); and J. Heterocycl. Chem. 19, 542–544 (1982)].

The invention also relates to compositions, which contain the active substances of the formula I, for controlling nematodes which are harmful to plants and for preventive protection of infestation of plants by nematodes.

The present invention moreover additionally includes the preparation of nematicidal compositions, which comprises intimately mixing active substances of the formula I with one or more carriers and auxiliary ingredients described in this specification. It also relates to a method of treating plants, which comprises applying the compounds of the formula I or the novel compositions.

A preferred method of using an active substance of the formula I or a nematicidal composition containing at least one of these active substances is introduction into the soil. In this method, the location of the plants is treated with a liquid or solid preparation.

However, the compounds of the formula I can also be applied to seeds (dressing/coating), by either soaking the seeds in a liquid preparation of the active substance or coating them with a solid preparation. In special cases, other types of application are moreover possible, thus, for example, controlled treatment of the plant stem, buds or leaves.

Active substances of the formula I are usually employed in the form of formulated combinations and can be applied to the area or plant to be treated at the same time as or successively with other active substances. These other active substances can also include other compositions used in agriculture, which serve in their beneficial use for increasing production by promoting the growth of crop plants, such as fertilizers, herbicides, insecticides, fungicides, molluscicides and the like, or mixtures of several of these preparations, if appropriate together with other carriers, surfactants or other application-promoting additives conventionally used in the art of formulation.

Suitable carriers and additives can be solid or liquid and correspond to the expedient substances in the art of formulation, for example naturally occurring or regenerated mineral substances, solvents, dispersants, wetting agents, adhesives, thickeners, binders or fertilizers.

The compounds of the formula I are employed in non-modified form or, preferably, together with the auxiliaries conventionally used in the art of formulation. They are processed in a known manner, for example, to emulsion concentrates, directly sprayable or dilutable solutions, dilute emulsions, wettable powders, soluble powders, dusts or granules, by encapsulation in, for example, polymeric substances. The methods of use, such as spraying, dusting, scattering or watering, like the nature of the compositions, is chosen according to the intended aims and the given circumstances. Favourable application amounts are in general 500 g to 6 kg of active substance (AS) per ha; preferably 1 to 4 kg of AS/ha.

The formulations, i.e. the compositions, preparations or combinations containing the active substance of the formula I and if appropriate a solid or liquid additive, are prepared in a known manner, for example by intimately mixing and/or grinding the active substances with extenders, for example with solvents or solid carriers, and if appropriate with surface-active substances (surfactants).

Possible solvents are: aromatic hydrocarbons, preferably the fractions $C_8$ to $C_{12}$, for example xylene mixtures or substituted naphthalenes, phthalic acid esters, such as dibutylphthalate or dioctylphthalate, aliphatic hydrocarbons, such as cyclohexane or paraffins, alcohols and glycols and ethers and esters thereof, such as ethanol, ethylene glycol and ethylene glycol monomethyl or monoethyl ether, ketones, such as cyclohexanone, strongly polar solvents, such as N-methyl-2-pyrrolidone, dimethylsulfoxide or dimethylformamide, and if appropriate epoxidized vegetable oils, such as epoxidized coconut oil or soya oil; or water.

Solid carriers, for example for dusts and dispersable powders, which are used are as a rule naturally occurring rock powders, such as calcite, talc, kaolin, montmorillonite or attapulgite. It is also possible to add highly disperse silicic acid or highly disperse absorbent polymers in order to improve the physical properties. Possible granular adsorptive granule carriers are porous grades, for example pumice, crushed brick, sepiolite or bentonite, and possible non-absorbent carrier materials are, for example, calcite or sand. A large number or pregranulated materials of inorganic or organic nature, such as, in particular, dolomite or comminuted plant residues, can moreover be used.

Possible surface-active substances are nonionic, cationic and/or anionic surfactants with good emulsifying, dispersing and wetting properties, depending on the nature of the active substance of the formula I to be formulated. By surfactants there are also to be understood surfactant mixtures.

Suitable inorganic surfactants can be either so-called water-soluble soaps or water-soluble synthetic surface-active compounds.

Soaps which may be mentioned are the alkali metal, alkaline earth metal or unsubstituted or substituted ammonium salts of higher fatty acids ($C_{10}$–$C_{22}$), for example the Na or K salts of oleic or stearic acid, or of naturally occurring fatty acid mixtures, which can be obtained, for example, from coconut oil or tallow oil. The fatty acid methyl-laurin salts and modified and non-modified phospholipids can furthermore also be mentioned.

However, so-called synthetic surfactants, in particular fatty sulfonates, fatty sulfates, sulfonated benzimidazole derivatives or alkylsulfonates, are more often used.

The fatty alcohol sulfonates or sulfates are as a rule in the form of alkali metal, alkaline earth metal or unsubstituted or substituted ammonium salts and contain an alkyl radical having 8 to 22 C atoms, alkyl also including the alkyl part of acyl radicals, for example the Na or Ca salt of lignin-sulfonic acid, of dodecylsulfuric acid ester or of a fatty alcohol sulfate mixture prepared from naturally occurring fatty acids. These also include the salts of sulfuric acid esters and sulfonic acids of fatty alcohol-ethylene oxide adducts. The sulfonated benzimidazole derivatives preferably contain two sulfonic acid groups and a fatty acid radical having 8–22 C atoms. Alkylarylsulfonates are, for example, the Na, Ca or triethanolamine salts of dodecylbenzenesulfonic acid, of dibutylnaphthalenesulfonic acid or of a naphthalenesulfonic acid-formaldehyde condensation product.

Corresponding phosphates, for example salts of the phosphoric acid ester of a p-nonylphenol-(4-14)-ethyleneoxide adduct, are furthermore also possible.

Possible nonionic surfactants are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl radical of the alkylphenols.

Other suitable nonionic surfactants are the water-soluble adducts, containing 20 to 250 ethylene glycol ether groups and 10 to 100 propylene glycol ether groups, of polyethylene oxide with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit.

Examples which may be mentioned of nonionic surfactants are nonylphenolpolyethoxyethanols, castor oil polyglycol ethers, polypropylene-polyethyleneoxide adducts, tributylphenoxypolyethyleneethanol, polyethylene glycol and octylphenoxypolyethoxyethanol.

Fatty acid esters of polyoxyethylene sorbitan, such as polyoxyethylene sorbitan trioleate, are furthermore also possible.

The cationic surfactants are, in particular, quaternary ammonium salts which contain at least one alkyl radical having 8 to 22 C atoms as N substituents and contain lower non-halogenated or halogenated alkyl or benzyl radicals or lower hydroxyalkyl radicals as further substituents.

The salts are preferably in the form of halides, methylsulfates or ethylsulfates, for example stearyltrimethylammonium chloride or the benzyldi(2-chloroethyl)ethylammonium bromide.

The surfactants conventionally used in the art of formulation are described, inter alia, in the following publications:

"Mc Cutcheon's Detergents and Emulsifiers Annual" MC Publishing Corp., Ridgewood, N.J., 1979; and Dr. Helmut Stache "Tensid Taschenbuch (Surfactant Handbook)", Carl Hanser Verlag Munich/ Vienna.

The agrochemical preparations as a rule contain 0.1 to 99% by weight, in particular 0.1 to 95% by weight, of active substance of the formula I, 99.9 to 1% by weight, in particular 99.8 to 5% by weight, of a solid or liquid additive and 0 to 25% by weight, in particular 0.1 to 25% by weight, of a surfactant.

Whereas concentrated compositions are rather preferred as commercial goods, the end user as a rule uses dilute compositions.

The compositions can also contain other additives, such as stabilizers, foam suppressants, viscosity regulators, binders, adhesives and fertilizers, or other active substances in order to achieve specific effects.

The present invention relates to such agrochemical compositions.

The following examples serve to illustrate the invention in more detail, without limiting it.

1. PREPARATION EXAMPLES

H.1

2-Difluoromethylthio-5-(4-chlorophenoxymethyl)-1,3,4-thiadiazole (Compound No. 1.3)

2 g of potassium hydroxide are dissolved in 8 ml of water and the solution is diluted with 30 ml of dioxane. 5.2 g of 2-mercapto-5-(4-chlorophenoxymethyl)-1,3,4-thiadiazole are added, while stirring. After addition of 0.1 g of potassium iodide and 0.1 g of tetrabutylammonium bromide, chlorodifluoromethane is passed in at a bath temperature of 40° C., always with vigorous stirring, until the uptake has ended. The reaction mixture is evaporated in vacuo, the residue is taken up in methylene chloride and the mixture is washed with water and with 1 N sodium hydroxide solution in succession. After evaporation of the solvent, the title compound is obtained in crystalline form of melting point 56°–57° C. (from ether).

H.2

2-(3,4,4-Trifluoro-3-buten-1-ylthio)-5-(1'-thiomethylmethyl)-1,3,4-oxadiazole (Compound No. 2.1)

3.3 g of 2-mercapto-5-methoxymethyl-1,3,4-oxadiazole are stirred together with 2.3 g of potassium t-butylate in a mixture of 25 ml of dioxane and 5 ml of dimethylformamide. 4.5 g of 4-bromo-1,1,2-trifluorobut-1-ene are added dropwise at room temperature and the mixture is subsequently stirred at room temperature for a further few hours. After customary working up, 3.8 g of the title compound are obtained in the form of an oil, $n_D^{27} = 1.5091$.

H.3

2-(3,4,4-trifluoro-3-buten-1-ylthio)-5-(tetrahydrofuran-2-yl)-1,3,4-oxadiazole (Compound No. 3.6)

2.1 g (0.019 mol) of potassium t-butylate are introduced into a solution of 3.2 g (0.018 mol) of 2-mercapto-5-(tetrahydrofuran-2-yl)-1,3,4-oxadiazole in a mixture of 80 ml of 1,4-dioxane and 10 ml of dimethylformamide. 4.9 g (0.026 mol) of 1-bromo-3,4,4-trifluoro-3-butene are then added dropwise at 25° C. and the reaction mixture is stirred at room temperature for 16 hours. The solvent mixture is distilled off under reduced pressure and the residue is dissolved in ethyl acetate. This solution is extracted with water, ice-cold 1 N sodium hydroxide solution and water in succession, dried with sodium sulfate and filtered and the solvent is distilled off under reduced pressure. 80.43 g of the desired product are obtained as a yellow oil ($n_D^{27} = 1.4904$).

The following compounds according to the invention can be prepared analogously to the above preparation examples and the processes already described (Tables 0–3). The compounds listed below serve to illustrate the present invention and do not represent a limitation thereof.

TABLE 0

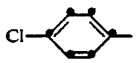

| Comp. No. | $R_3$ | $R_2$ | $X_1$ | $X_2$ | Physic. Data |
|---|---|---|---|---|---|
| 0.1 | $CH_3$ | H | O | S | m.p. 77–79° C. |
| 0.2 | H | H | O | S | m.p. 115–120° C. |
| 0.3 | Cl—⟨⟩— | H | O | S | m.p. 155–158° C. |
| 0.4 | $CH_3$ | H | S | O | m.p. 67–69° C. |

TABLE 1

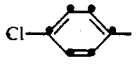

| Comp. No. | $R_3$ | $R_2$ | $X_1$ | $X_2$ | Physic. Data |
|---|---|---|---|---|---|
| 1.1 | $CH_3$ | H | O | S | $n_D^{22} = 1.5182$ |
| 1.2 | H | H | O | S | $n_D^{22} = 1.5308$ |
| 1.3 | Cl—⟨⟩— | H | O | S | m.p. 56–57° C. |
| 1.4 | $CH_3$ | H | S | O | $n_D^{25} = 1.5219$ |

TABLE 2

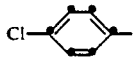

| Comp. No. | $R_3$ | $R_2$ | $X_1$ | $X_2$ | Physic. Data |
|---|---|---|---|---|---|
| 2.1 | $CH_3$ | H | S | O | $n_D^{27} = 1.5091$ |
| 2.2 | H | H | O | S | |
| 2.3 | $CH_3$ | H | O | S | $n_D^{22} = 1.5125$ |
| 2.4 | Cl—⟨⟩— | H | O | S | $n_D^{22} = 1.5498$ |

TABLE 3

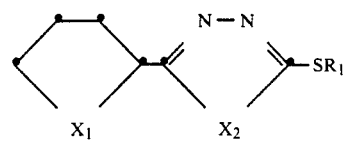

| Comp. No. | $R_1$ | $X_1$ | $X_2$ | Physic. Data |
|---|---|---|---|---|
| 3.1. | $-CHF_2$ | O | S | $n_D^{23} = 1.5373$ |
| 3.2. | $-CHF_2$ | O | O | $n_D^{23} = 1.4940$ |
| 3.3. | $-CHF_2$ | S | O | |

TABLE 3-continued

| Comp. No. | $R_1$ | $X_1$ | $X_2$ | Physic. Data |
|---|---|---|---|---|
| 3.4. | $-CHF_2$ | S | S | |
| 3.5. | $-CH_2CH_2CF=CF_2$ | O | S | |
| 3.6. | $-CH_2CH_2CF=CF_2$ | O | O | $n_D^{23} = 1.4904$ |
| 3.7. | $-CH_2CH_2CF=CF_2$ | S | O | oil |
| 3.8. | $-CH_2CH_2CF=CF_2$ | S | S | $n_D^{50} = 1.5831$ |

F. FORMULATION EXAMPLES

F.2. Formulation examples for liquid active substances of the formula I (%=percent by weight)

| 2.1 Emulsion concentrates | (a) | (b) | (c) |
|---|---|---|---|
| Active substance from Tables 0–3 | 25% | 40% | 50% |
| Ca dodecylbenzenesulfonate | 5% | 8% | 6% |
| Castor oil polyethylene glycol ether (36 mol of ethylene oxide) | 5% | — | — |
| Tributylphenolpolyethyleneglycol ether (30 mol of ethylene oxide) | — | 12% | 4% |
| Cyclohexanone | — | 15% | 20% |
| Xylene mixture | 65% | 25% | 20% |

Emulsions of any desired concentration can be prepared from such concentrate by dilution with water.

| 2.2 Solutions | (a) | (b) | (c) | (d) |
|---|---|---|---|---|
| Active substance from Tables 0–3 | 80% | 10% | 5% | 95% |
| Ethylene glycol monomethyl ether | 20% | — | — | — |
| Polyethylene glycol MW 400 | — | 70% | — | — |
| N-Methyl-2-pyrrolidone | — | 20% | — | — |
| Epoxidized coconut oil | — | — | 1% | 5% |
| Benzine (boiling limits 160–190° C.) | — | — | 94% | — |

(MW = molecular weight)

The solutions are suitable for use in the form of tiny drops.

| 2.3 Granules | (a) | (b) |
|---|---|---|
| Active substance from Tables 0–3 | 5% | 10% |
| Kaolin | 94% | — |
| Highly disperse silicic acid | 1% | — |
| Attapulgite | — | 90% |

The active substance is dissolved in methylene chloride, the solution is sprayed onto the carrier and the solvent is then evaporated off in vacuo.

| 2.4 Dusts | (a) | (b) |
|---|---|---|
| Active substance from Tables 0–3 | 2% | 5% |
| Highly disperse silicic acid | 1% | 5% |
| Talc | 97% | — |
| Kaolin | — | 90% |

Ready-to-use dusts are obtained by intimately mixing the carriers with the active substance.

F.3 Formulation examples for solid active substances of the formula I (%=percent by weight)

| 3.1 Wettable powders | (a) | (b) | (c) |
|---|---|---|---|
| Active substance from Tables 0-3 | 25% | 50% | 75% |
| Na ligninsulfonate | 5% | 5% | — |
| Na lauryl sulfate | 3% | — | 5% |
| Na diisobutylnaphthalenesulfonate | — | 6% | 10% |
| Octylphenolpolyethylene glycol ether (7-8 mol of ethylene oxide) | — | 2% | — |
| Highly disperse silicic acid | 5% | 10% | 10% |
| Kaolin | 62% | 27% | — |

The active substance is mixed thoroughly with the additives and the mixture is ground thoroughly in a suitable mill. Wettable powders which can be diluted with water to give suspensions of any desired concentration are obtained.

| 3.2 Emulsion concentrate | |
|---|---|
| Active substance from Tables 0-3 | 10% |
| Octylphenol polyethylene glycol ether (4-5 mol of ethylene oxide) | 3% |
| Ca dodecylbenzenesulfonate | 3% |
| Castor oil polyglycol ether (35 mol of ethylene oxide) | 4% |
| Cyclohexanone | 30% |
| Xylene mixture | 50% |

Emulsions of any desired concentration can be prepared from this concentrate by dilution with water.

| 3.3 Dusts | (a) | (b) |
|---|---|---|
| Active substance from Tables 0-3 | 5% | 8% |
| Talc | 95% | — |
| Kaolin | — | 92% |

Ready-to-use dusts are obtained by mixing the active substance with the carriers and grinding the mixture on a suitable mill.

| 3.4 Extruder granules | |
|---|---|
| Active substance from Tables 0-3 | 10% |
| Na lignin sulfonate | 2% |
| Carboxymethylcellulose | 1% |
| Kaolin | 87% |

The active substance is mixed with the additives and the mixture is ground and moistened with water. This mixture is extruded and then dried in a stream of air.

| 3.5 Coated granules | |
|---|---|
| Active substance from tables 0-3 | 3% |
| Polyethylene glycol (MW 200) | 3% |
| Kaolin | 94% |
| (MW = molecular weight) | |

The finely ground active substance is uniformly applied to the kaolin moistened with polyethylene glycol in a mixer. Dust-free coated granules are obtained in this manner.

| 3.6 Suspension concentrate | |
|---|---|
| Active substance from Tables 0-3 | 40% |
| Ethylene glycol | 10% |

-continued

| 3.6 Suspension concentrate | |
|---|---|
| Nonylphenol polyethylene glycol ether (15 mol of ethylene oxide) | 6% |
| Na ligninsulfonate | 10% |
| Carboxymethylcellulose | 1% |
| 37% Aqueous formaldehyde solution | 0.2% |
| Silicone oil in the form of a 75% aqueous emulsion | 0.8% |
| Water | 32% |

The finely ground active substance is intimately mixed with the additives. A suspension concentrate from which suspensions of any desired concentration can be prepared by dilution with water is thus obtained.

B. BIOLOGICAL EXAMPLE

B.3.1 Action against Meloidogyne incognita on tomatoes

Eggs of Meloidogyne incognita are mixed into sand. This mixture is then introduced into clay pots of 200 ml capacity (5000 eggs per pot). On the same day, one tomato plant 3 weeks old is planted per pot and the formulated active substance is introduced into the pots by means of drench application (0.0006% of active substance, based on the volume of soil). The potted plants are now placed in a greenhouse at a temperature of 26±1° C. and a relative atmospheric humidity of 60%. After 4 weeks have elapsed, evaluation is performed by examining the plants for root knot formation in accordance with the so-called root knot index.

Compounds from Table 1 have a good activity against Meloidogyne incognita, by substantial reduction of the root knot formation. In contrast, untreated but infected control plants show severe root knot formation (=100%). Thus, for example, the compounds No. 1.1, 1.3, 3.2, 3.6, 3.7 and 3.8 inhibit root knot formation almost completely in the above experiment (0-10% residual infestation).

What is claimed is:

1. A 2-Mercapto-1,3,4-oxadiazole and 2-mercapto-1,3,4-thiadiazole of the formula I

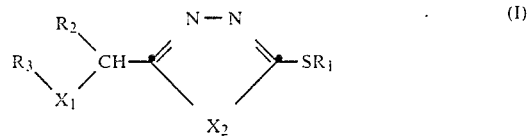

in which $X_1$ and $X_2$ independently of one another are oxygen or sulfur, $R_1$ is difluoromethyl or 3,4,4-trifluoro-3-buten-1-yl, $R_2$ is hydrogen or $C_1$-$C_3$ alkyl and $R_3$ is hydrogen, $C_1$-$C_5$ alkyl which is unsubstituted or substituted by halogen or $C_1$-$C_3$ alkoxy, $C_3$-$C_7$ alkenyl which is unsubstituted or substituted by halogen or $C_1$-$C_3$ alkoxy, $C_3$-$C_7$ alkynyl which is unsubstituted or substituted by halogen or $C_1$-$C_3$ alkoxy, or phenyl which is unsubstituted or substituted by halogen, $NO_2$, $CF_3$, $C_1$-$C_3$-alkyl or $C_1$-$C_3$ alkoxy, or wherein, furthermore, $R_2$ and $R_3$ together can form the methylene chain (—$CH_2$—)ñ as a constituent of a 5- or 6-membered ring with the heteroatom $X$:, in which n is 3 or 4.

2. A 2-mercapto-1,3,4-oxadiazole of the formula Ia

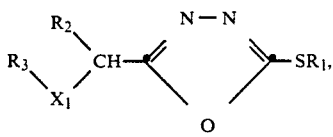

according to claim 1, in which $R_1$ is difluoromethyl, $R_2$ is hydrogen and $R_3$ is methyl, or in which $R_2$ and $R_3$ together form the methylene chain $(-CH_2-)_3$, as a constituent of a tetrahydrofuran-2-yl or tetrahydrothienyl ring.

3. 2-Difluoromethylthio-5-(tetrahydrofuran-2-yl)-1,3,4-oxadiazole according to claim 2.

4. A 2-mercapto-1,3,4-oxadiazole of the formula Ia

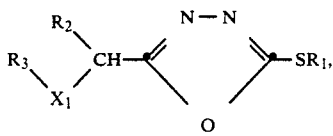

according to claim 1, in which $R_1$ is 3,4,4-trifluoro-3-buten-1-yl, $R_2$ is hydrogen and $R_3$ is methyl, or in which $R_2$ and $R_3$ together form the methylene chain $(-CH_2-)_3$, as a constituent of a tetrahydrofuran-2-yl or tetrahydrothienyl ring.

5. 2-(3,4,4-Trifluoro-3-buten-1-ylthio)-5-(tetrahydrofuran-2-yl)-1,3,4-oxadiazole according to claim 4.

6. A 2-mercapto-1,3,4-thiadiazole of the formula Ib

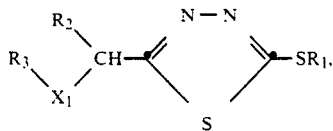

according to claim 1, in which $R_1$ is difluoromethyl, $R_2$ is hydrogen and $R_3$ is $C_1-C_3$ alkyl which is unsubstituted or substituted by halogen, or phenyl which is unsubstituted or substituted by halogen.

7. 2-Difluoromethylthio-5-methoxymethyl-1,3,4-thiadiazole according to claim 6.

8. 2-Difluoromethylthio-5-(4-chlorophenoxymethyl)-1,3,4-thiadiazole according to claim 6.

9. A pest control composition for controlling or preventing infestation of plants by nematodes, which contains at least one compound of the formula I according to claim 1 as the active component.

10. A composition according to claim 9, which contains 2-difluoromethylthio-5-methoxymethyl-1,3,4-thiadiazole as the active component.

11. A composition according to claim 9, which contains 2-(3,4,4-trifluoro-3-buten-1-ylthio)-5-(tetrahydrofuran-2-yl)-1,3,4-oxadiazole as the active component.

12. A composition according to claim 9, which contains 0.1 to 95% of an active substance of the formula I, 99.8 to 5% of a solid or liquid additive and 0.1 to 25% of a surfactant.

13. A method of controlling or preventing infestation of crop plants by nematodes, which comprises applying a compound of the formula I according to claim 1 to the plant or its location.

14. A method according to claim 13 wherein the nematodes are of the genus Meloidogyne, Heterodera or Globodera.

15. A composition according to claim 9, which contains 0.1 to 99% of a substance of the formula I, 99.9 to 1% of a solid or liquid additive and 0 to 25% of a surfactant.

16. A composition of claim 9 which contains, as the active component, a compound of the formula

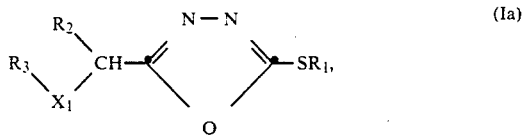

in which $R_1$ is difluoromethyl, $R_2$ is hydrogen and $R_3$ is methyl, or in which $R_2$ and $R_3$ together form the methylene chain $(-CH_2-)_3$, as a constituent of a tetrahydrofuran-2-yl or tetrahydrothienyl ring.

17. A method of claim 13 which comprises applying to the plant or its location compound of the formula

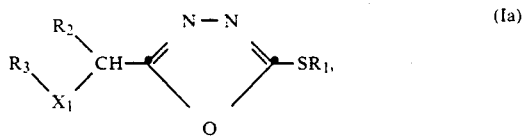

according to claim 1, in which $R_1$ is difluoromethyl, $R_2$ is hydrogen and $R_3$ is methyl, or in which $R_2$ and $R_3$ together form the methylene chain $(-CH_2-)_3$, as a constituent of a tetrahydrofuran-2-yl or tetrahydrothienyl ring.

* * * * *